United States Patent

Hötzel et al.

[11] Patent Number: 5,549,804
[45] Date of Patent: Aug. 27, 1996

[54] ARRANGEMENT FOR DETECTING THE OXYGEN CONTENT IN THE EXHAUST GAS OF AN INTERNAL COMBUSTION ENGINE

[75] Inventors: Gerhard Hötzel, Stuttgart; Harald Neumann, Vaihingen; Walter Strassner, Schorndorf; Johann Riegel, Bietigheim-Bissingen, all of Germany

[73] Assignee: Robert Bosch GmbH, Stuttgart, Germany

[21] Appl. No.: 315,970

[22] Filed: Sep. 30, 1994

[30] Foreign Application Priority Data

Sep. 30, 1993 [DE] Germany ............ 43 33 229.3

[51] Int. Cl.$^6$ ................................ G01N 27/26
[52] U.S. Cl. ................... 204/425; 204/426; 204/427; 205/784.5
[58] Field of Search ............... 204/153.18, 421–429; 205/784, 784.5

[56] References Cited

U.S. PATENT DOCUMENTS

| 4,207,159 | 6/1980 | Kimura et al. | 204/425 |
|---|---|---|---|
| 4,464,244 | 8/1984 | Uchida et al. | 204/426 |
| 4,498,968 | 2/1985 | Yamada et al. | 204/426 |
| 4,755,274 | 7/1988 | Mase et al. | 204/429 |
| 5,028,309 | 7/1991 | Nishizawa et al. | 204/425 |

FOREIGN PATENT DOCUMENTS

| 0172746 | 2/1986 | European Pat. Off. |
| 0194082 | 9/1986 | European Pat. Off. |
| 2276458 | 9/1994 | United Kingdom |

Primary Examiner—T. Tung
Attorney, Agent, or Firm—Walter Ottesen

[57] ABSTRACT

The invention is directed to an arrangement for detecting the oxygen content in the exhaust gas of an internal combustion engine. The arrangement includes a concentration measuring cell operating pursuant to the Nernst principle. The concentration measuring cell has a measuring electrode, a solid electrolyte and a reference electrode and a series circuit which includes a direct voltage source and a series resistor. The series circuit connects the measuring electrode to the reference electrode. The measuring electrode communicates with the exhaust gas of the internal combustion engine and is connected to the reference electrode via the solid electrolyte. The reference electrode communicates with the reference gas volume. The reference gas volume is partitioned from the exhaust gas and from the ambient air so that a particle exchange between the reference gas volume and the exhaust gas as well as between the reference gas volume and the ambient air is at least made more difficult. The output voltage of the concentration measuring cell defines a measure for the difference of the oxygen concentrations in the exhaust gas of the engine and the reference gas volume. The output voltage of the direct voltage source and/or the value of the series resistance is so pregiven that an electric current Ip is always so directed that oxygen is transported from the exhaust gas to the reference gas volume independently of the output voltage of the concentration measuring cell. The current Ip flows in a current circuit including direct voltage source, series resistance and concentration measuring cell.

2 Claims, 1 Drawing Sheet

ARRANGEMENT FOR DETECTING THE OXYGEN CONTENT IN THE EXHAUST GAS OF AN INTERNAL COMBUSTION ENGINE

FIELD OF THE INVENTION

The invention relates to an arrangement for detecting the oxygen content in the exhaust gas of an internal combustion engine which is utilized as the drive unit for a motor vehicle.

BACKGROUND OF THE INVENTION

It is known to measure the oxygen content of exhaust gases with the aid of a concentration cell, for example, made of $ZrO_2$ ceramic, with respect to a reference oxygen content in a reference atmosphere. The reference atmosphere can, for example, be defined by the ambient air or also by a reference gas in a volume closed off or virtually closed off with respect to the ambient. A stable oxygen atmosphere is achieved in this volume, for example, in that oxygen is pumped out of the exhaust gas into the volume by impressing a current. Such a pump reference atmosphere affords the advantage with respect to an ambient air reference that an adulteration of the reference gas atmosphere is comparatively slight. Adulteration of the reference atmosphere can, for example, be caused by water spray or fuel vapor in direct proximity of the arrangement. In general, the reference volumes are selected to be very small and are not gas tight with respect to the ambient, for example, because of residual porosity of the $ZrO_2$ ceramic or because gas channels are deliberately built in which are intended to avoid gas pressures in the reference volume which are too high. For this reason, a stable reference atmosphere can only be maintained with a permanently impressed current.

However, this is associated with the disadvantage that a decomposition of the electrolyte can occur because of the applied voltage which is needed. This decomposition of the electrolyte can especially occur when exhaust gas is produced from the combustion of a fuel-rich mixture and the exhaust gas has a correspondingly low content of oxygen.

Furthermore, a temperature-dependent change of the measuring signal occurs when the pump voltage is applied to the electrolyte via the measuring electrodes. The measuring signal Us is taken off from the measuring electrode at the exhaust-gas end and a reference electrode at the reference-gas end. In this case, the measuring signal Us is comprised additively from the Nernst voltage Un and a voltage excursion Ri*Ip. The Nernst voltage Un results because of the differing oxygen partial pressures at the electrolyte. Ri represents the internal resistance of the electrolyte and Ip identifies the pump current flowing as a consequence of the pump voltage. The product Ri*Ip essentially defines a temperature-dependent disturbance of the measurement signal because of the temperature dependence of the probe internal resistance Ri.

SUMMARY OF THE INVENTION

In view of this background, it is an object of the invention to provide an arrangement for measuring the oxygen content in the exhaust gas of an internal combustion engine. The arrangement operates with an almost completely closed reference gas volume without the above-mentioned disadvantages, namely, decomposition of the electrolyte and the occurrence of large disturbances of the measurement signal because of the temperature dependency of the internal resistance of the electrolyte.

The invention achieves the above object with a concentration measuring cell operating pursuant to the Nernst principle. The measuring cell has a measuring electrode, a solid electrolyte and a reference electrode and a series circuit comprising a direct-current voltage source Uv and a series resistor Rv which connects the measuring electrode to the reference electrode. The measuring electrode communicates with the exhaust gas of the engine and is connected to the reference electrode, which communicates with a reference gas volume, via the solid electrolyte. The reference gas volume is so separated from the exhaust gas and from the ambient air that a particle exchange between the reference gas volume and the exhaust gas as well as between the reference gas volume and the ambient air is impeded. The output voltage of the concentration measuring cell defines a measure for the difference of the oxygen concentration in the exhaust gas of the engine and in the reference gas volume. The output voltage of the direct-voltage source and/or the value of the series resistance are so determined that an electric current Ip is always so directed that oxygen from the exhaust gas is transported to the reference gas volume. The electric current Ip flows in a current circuit comprising direct-current voltage source, series resistor and concentration measuring cell. A very low net current flow results in rich exhaust gas or high probe voltage and, for lean exhaust gas or low probe voltage, a clearly higher net current flow results.

The arrangement of the invention effects a weakening of the temperature dependency of the probe signal Us=Un+Ri*Ip especially for a rich mixture composition and prevents a possible decomposition of the electrolyte as is the case for low oxygen content in the exhaust gas (rich mixture composition) and high pump current.

An adulterated reference can occur, for example, as a consequence of the penetration of fuel vapors into the reference gas volume when the motor vehicle is at standstill. A further advantage of the invention is seen in that an automatic elimination of this adulteration takes place because, during adulteration, a clearly reduced probe voltage results which generates an increased net current flow.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
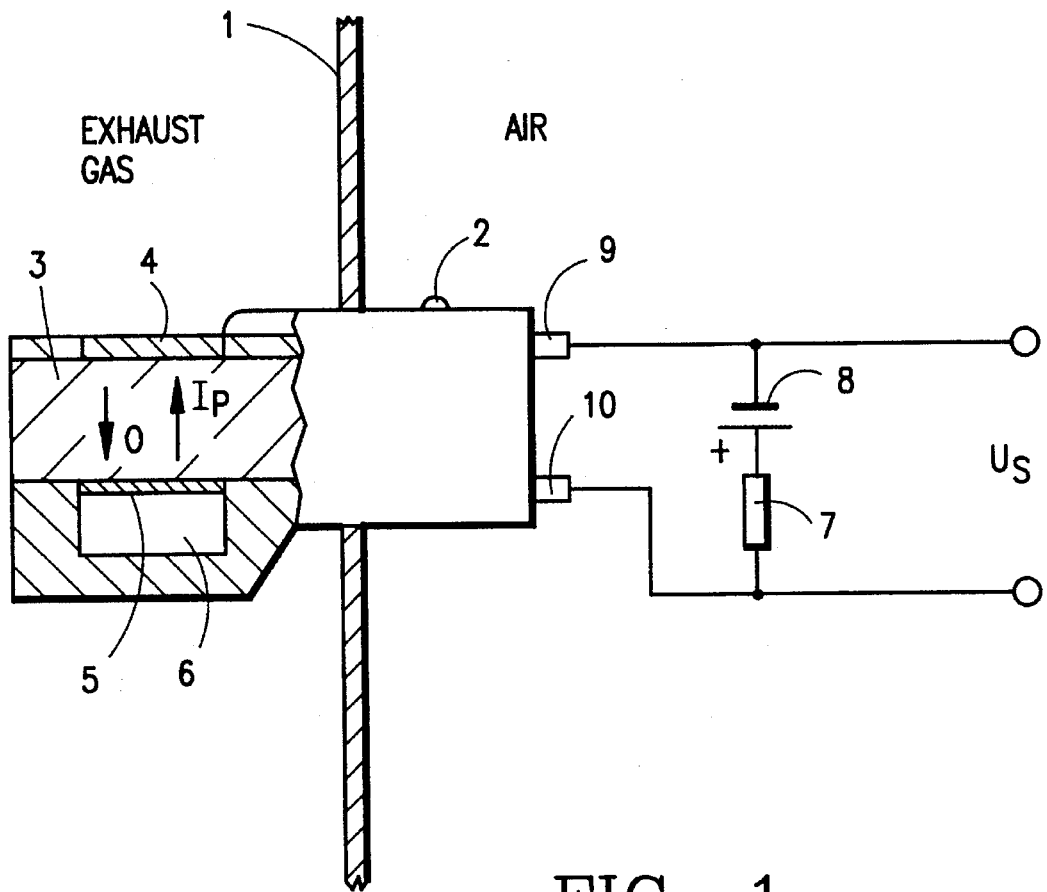
FIG. 1 shows an embodiment of the arrangement of the invention.

FIG. 1 shows an exhaust-gas probe 2, in section, mounted in an exhaust-gas pipe of which a wall 1 is shown. This wall partitions the exhaust gas of an internal combustion engine (to the left) from the ambient air (to the right). The exhaust-gas probe includes a solid electrolyte 3 in its exhaust-gas end portion. This solid electrolyte 3 is between a measuring electrode 4 subjected to the exhaust gas and a reference electrode 5. A reference gas volume 6 communicates with the measuring electrode 5 and is neither in direct contact with the exhaust gas nor with the ambient air. An overpressure can possibly build up in the reference gas volume and decays via an indirect connection to the ambient air such as via a measurement input line 10 configured to be porous. The input line 10 is connected to the reference electrode and an input line 9 is connected to the measuring electrode. A direct-current voltage source 8 (Uv) and a series resistor 7 (Rv) are connected between the input line 10 and the input line 9. The measuring voltage signal Us of this arrangement is taken off between the input lines 9 and 10.

Figure 2:
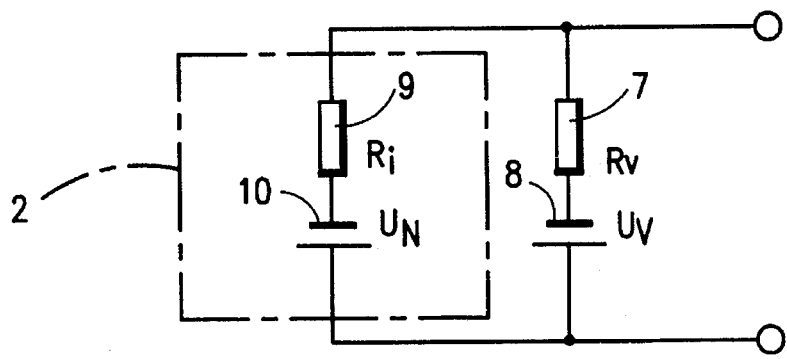
FIG. 2 is a representation of an equivalent electric circuit.

FIG. 2 shows an equivalent circuit of the arrangement according to the invention wherein the electrolyte 3 and the electrodes 4 and 5 are shown as voltage source Un (10) and resistance Ri (9).

The direct voltage source produces a pump current Ip through the electrolyte. The electrolyte, in combination with the internal resistance Ri of the electrolyte, produces a voltage excursion Ri*Ip. The concentration cell is configured from the electrolyte and the electrodes and produces a Nernst voltage Un. At constant temperature, this Nernst voltage Un is dependent upon the logarithm of the quotient of the partial pressures in the reference gas volume and in the exhaust gas. The measurement voltage signal Us is composed additively of two components, namely: Uv−Un=Ip*(Rv+Ri). The pump current Ip is then so directed that it transports oxygen from the exhaust gas to the reference gas volume. A drop of the oxygen partial pressure in the reference gas volume is countered in this manner. Advantageously, the value of the counter voltage Uv is so selected that it lies just above the highest possible Nernst voltage Un of the concentration cell.

The table below shows how the pump current Ip changes in dependence upon the mixture composition and the probe temperature for an embodiment of the arrangement according to the invention having an Rv value of 51 kohm and a prevoltage of 1 Volt. The Nernst voltage Un=0.9 Volt then indicates a rich mixture and the Nernst voltage of 0.1 Volt indicates a lean mixture. The probe internal resistance Ri=100 ohm is typical for a hot probe and the internal resistance of 10,000 ohm is typical for a cold probe. The values of Us and Ip are computed from the relationships: Ip=(Uv−Un)/(Rv+Ri) and Us=Un+Ri*Ip.

| Ri [ohm] | Rv [kohm] | Uv [V] | Un | Us [V] | Ip [µA] |
| --- | --- | --- | --- | --- | --- |
| 100 | 51.0 | 1.0 | 0.9 | 0.900 | 2.0 |
| 100 | 51.0 | 1.0 | 0.1 | 0.102 | 17.6 |
| 10,000 | 51.0 | 1.0 | 0.9 | 0.916 | 1.6 |
| 10,000 | 51.0 | 1.0 | 0.1 | 0.248 | 14.8 |

The advantages mentioned above occur because of the relationships explained below.

First, the arrangement according to the invention reduces the temperature dependency of the probe signal Us=Un+Ri*Ip in that the temperature-dependent variation of the probe internal resistance Ri leads, as part of the pump flow circuit, to a counter change of the pump current Ip so that the effect of the probe internal resistance change on the voltage excursion Ri*Up is reduced.

A possible decomposition of the electrolyte for low oxygen content in the exhaust gas (rich mixture composition) is countered in that, for the circuit of the invention, the pump current Ip is proportional to the difference of the series voltage Uv and the Nernst voltage Un of the concentration cell. The value of this difference is small for a rich mixture because the low oxygen content in the exhaust gas leads to a high Nernst voltage. In this way, the pump current is substantially a function of the mixture composition so that in the critical case of a rich mixture, a comparatively low current flows and, in the critical case of a lean mixture, a higher current flows. The higher current effects an increased oxygen transport to the reference gas volume and prevents the oxygen partial pressure in the reference gas volume from dropping too far over the long term.

For an adulterated reference, the oxygen partial pressure in the reference gas volume can drop below the value of the oxygen partial pressure in the exhaust gas. For example, for a motor vehicle at standstill, fuel vapors can penetrate into the reference gas volume and bind the oxygen to a large extent. The Nernst voltage Un changes its sign when the partial pressure of the oxygen in the reference gas volume drops below the value of the oxygen partial pressure in the exhaust gas. In the arrangement of the invention, it is no longer the difference, but instead, the sum of the quantities of the series voltage Uv and the Nernst voltage Un which determines the intensity of the pump current Ip. In this way, the pump current increases and therewith the quantity of the oxygen which is transported from the exhaust gas to the reference gas volume. Finally, this affects to some degree a scavenging of the reference gas volume with oxygen which leads to an elimination of the adulteration of the reference.

It is understood that the foregoing description is that of the preferred embodiments of the invention and that various changes and modifications may be made thereto without departing from the spirit and scope of the invention as defined in the appended claims.

What is claimed is:

1. An arrangement for detecting the oxygen content in the exhaust gas of an internal combustion engine for driving a motor vehicle, the exhaust gas containing gas particles, the arrangement comprising:

a concentration measuring cell operating pursuant to the Nernst principle and including:

a solid electrolyte;

a measuring electrode arranged on said electrolyte and exposed to said exhaust gas;

a reference electrode arranged on said electrolyte and being connected to said measuring electrode through said electrolyte;

an enclosed space on the side of the reference electrode opposite the side of the solid electrolyte to define a reference gas volume in contact with said reference electrode, said reference gas volume containing gas particles;

means for separating said reference gas volume from said exhaust gas and from ambient air containing gas particles so that an exchange of gas particles between said reference gas volume and said exhaust gas and between said reference gas volume and said ambient air is impeded;

said concentration measuring cell having an output voltage defining a measure for the difference of the oxygen concentration in said exhaust gas and said reference gas volume;

a series circuit connected across said measuring and reference electrodes and including a direct-current voltage source (Uv) and a resistor (Rv) connected in series with said direct-current voltage source (Uv);

said direct-current voltage source (Uv) having a source output voltage and said resistor (Rv) having a resistance value;

said direct-current voltage source (Uv), said resistor (Rv) and said concentration measuring cell conjointly defining a current loop through which a current (Ip) flows having a value dependent upon said oxygen content of said exhaust gas; and, said source output voltage and/or said resistance value being so predetermined that said current (Ip) flows through said current loop to always be so directed that oxygen is transported from said exhaust gas to said reference gas volume independently of said output voltage of said concentration measuring cell.

2. The arrangement of claim 1, wherein the magnitude of said direct-current voltage source (Uv) is less than 1.5 times the highest value of said output voltage of said concentration measuring cell when measured without said direct-current voltage source and said resistor.

* * * * *